United States Patent
Maile et al.

(10) Patent No.: US 9,214,799 B2
(45) Date of Patent: Dec. 15, 2015

(54) ELECTROSTATIC DISCHARGE PROTECTION CIRCUIT FOR IMPLANTABLE MEDICAL DEVICE

(71) Applicant: Cardiac Pacemakers, Inc., St. Paul, MN (US)

(72) Inventors: Keith R. Maile, New Brighton, MN (US); Lance E. Juffer, Lino Lakes, MN (US); William J. Linder, Golden Valley, MN (US); Ron A. Balczewski, Bloomington, MN (US); Nicholas J. Stessman, Minneapolis, MN (US); Mark Duane Jansen, Brooklyn Park, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 147 days.

(21) Appl. No.: 13/939,423

(22) Filed: Jul. 11, 2013

(65) Prior Publication Data

US 2014/0022678 A1 Jan. 23, 2014

Related U.S. Application Data

(60) Provisional application No. 61/673,330, filed on Jul. 19, 2012.

(51) Int. Cl.
*H02H 3/20* (2006.01)
*A61N 1/37* (2006.01)
*H02H 9/04* (2006.01)
*H01L 27/02* (2006.01)

(52) U.S. Cl.
CPC .............. *H02H 3/20* (2013.01); *A61N 1/3718* (2013.01); *H01L 27/0285* (2013.01); *H02H 9/046* (2013.01)

(58) Field of Classification Search
USPC .......................................................... 361/56
See application file for complete search history.

(56) References Cited

U.S. PATENT DOCUMENTS 6,052,623 A * 4/2000 Fenner et al. ................... 607/36
6,327,125 B1 12/2001 Colclaser et al.
(Continued)

FOREIGN PATENT DOCUMENTS

WO WO-2010062463 A1 6/2010
WO WO-2011139777 A2 11/2011
WO WO-2014014733 A1 1/2014

OTHER PUBLICATIONS

Ker, Ming-Dou, "Area-Efficient VDD-to-VSS ESD Clamp Circuit by Using Substrate-Triggering Field-Oxide Device (STFOD) for Whole-Chip ESD Protection", VLSI Technology, Systems, and Applications, 1997. Proceedings of Technical Papers. 1997 International Symposium on VLSI Design Department, Computer & Communication Research Laboratories (CCL) Industrial Technology Research Institute (ITN), Hsinchu, Taiw, (Jun. 3-5, 1997), 69-73.

(Continued)

*Primary Examiner* — Thienvu Tran
*Assistant Examiner* — Angela Brooks
(74) *Attorney, Agent, or Firm* — Schwegman Lundberg & Woessner, P.A.

(57) ABSTRACT

An implantable medical device can include an integrated circuit comprising an electrostatic discharge (ESD) protection circuit. The ESD protection circuit can include an active circuit, a first passive circuit, and a second passive circuit. For example, at least one of the first or second passive circuits can include an array of capacitors in a series configuration, a parallel configuration, or a combination of series and parallel configurations. The first and second passive circuits can be configured to establish a specified time constant, and, in response to an applied ESD, the first and second passive circuits can provide a control signal to active circuit to switch the active circuit from a substantially non-conductive mode to a substantially conductive mode.

20 Claims, 5 Drawing Sheets

(56) References Cited

U.S. PATENT DOCUMENTS

| | | | |
|---|---|---|---|
| 6,459,553 | B1 | 10/2002 | Drapkin et al. |
| 6,718,203 | B2* | 4/2004 | Weiner et al. .................... 607/2 |
| 7,187,530 | B2* | 3/2007 | Salling et al. ................. 361/111 |
| 7,659,497 | B2 | 2/2010 | Abadeer et al. |
| 8,610,188 | B2* | 12/2013 | Kerber et al. ................. 257/296 |
| 2005/0127444 | A1 | 6/2005 | Watanabe |
| 2009/0168280 | A1* | 7/2009 | Huang et al. .................... 361/56 |
| 2010/0321841 | A1* | 12/2010 | Worley et al. .................... 361/56 |
| 2012/0176710 | A1* | 7/2012 | Domanski et al. ............. 361/56 |
| 2012/0224284 | A1* | 9/2012 | Jalilizeinali et al. ............ 361/56 |
| 2013/0265676 | A1* | 10/2013 | Prabhu et al. ................... 361/56 |

OTHER PUBLICATIONS

Ker, Ming-Dou, et al., "Design of Low-Capacitance Bond Pad for High-Frequency I/O Applications in CMOS Integrated Circuits", (2000), 4 pgs.

Worley, E R, et al., "Sub-Micron Chip ESD Protection Schemes Which Avoid Avalanching Junctions", EOS/ESD Symposium 95-13, Rockwell Telecommunications 431 1 Jamboree Rd, Newport Beach, CA 92658-8902, (Sep. 12, 1995), 1.2.1-1.2.8.

"A retina stimulator ASIC with 232 electrodes, custom ESD production and active charge balancing", IEEE International Symposium on circuits and systems, (May 21, 2006), 4 pgs.

"International Application Serial No. PCT/US2013/050032, International Preliminary Report on Patentability mailed Jan. 29, 2015", 8 pgs.

"International Application Serial No. PCT/US2013/050032, International Search Report mailed Nov. 15, 2013", 4 pgs.

"International Application Serial No. PCT/US2013/050032, Written Opinion mailed Nov. 15, 2013", 6 pgs.

"On-chip ESD protection design for integrated circuits: an overview for IC designers", Microelectronics Journal, Mackintosh Publications ltd vol. 32, (Sep. 1, 2001), 733-747.

* cited by examiner

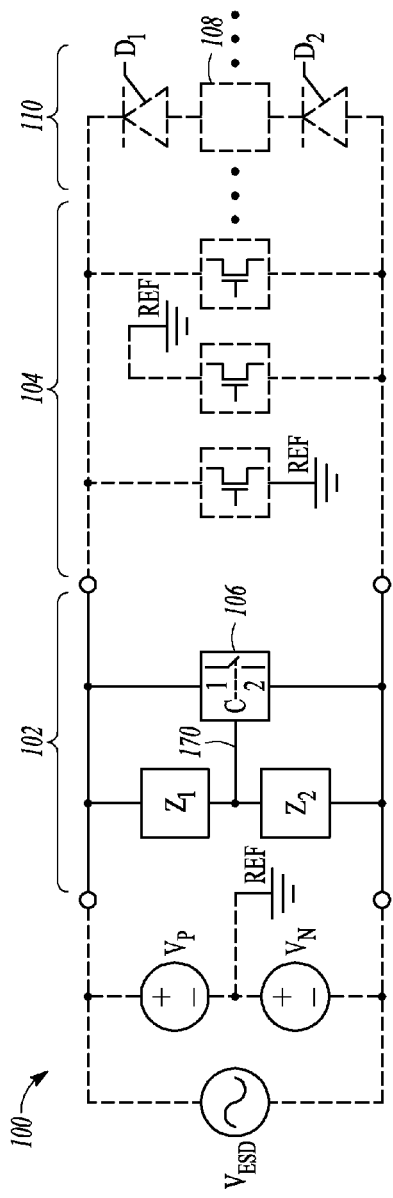
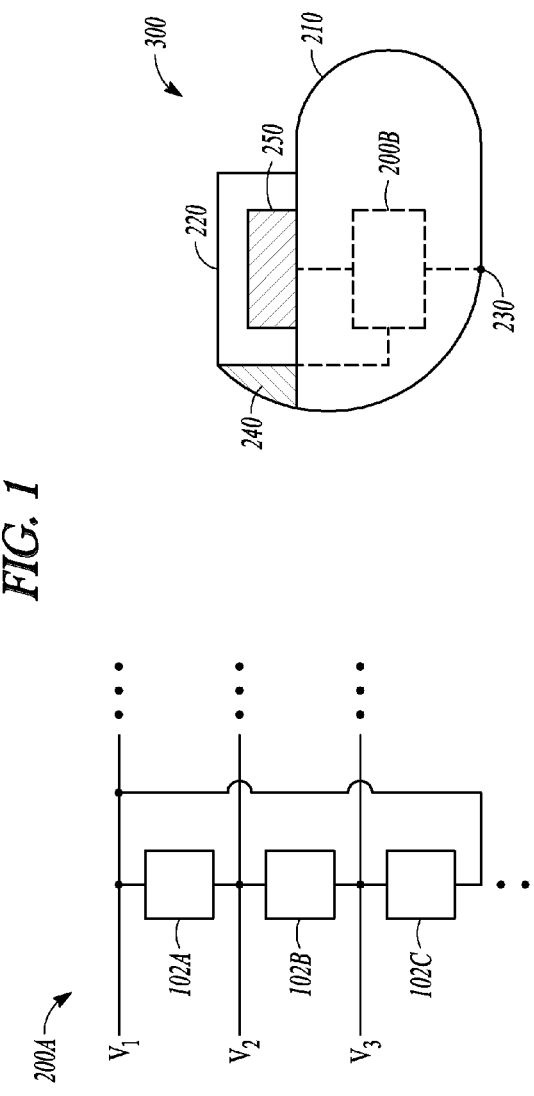
FIG. 1
FIG. 2
FIG. 3

ELECTROSTATIC DISCHARGE PROTECTION CIRCUIT FOR IMPLANTABLE MEDICAL DEVICE

CLAIM OF PRIORITY

This application claims the benefit of priority under 35 U.S.C. §119(e) of Maile et al., U.S. Provisional Patent Application Ser. No. 61/673,330, titled "ELECTROSTATIC DISCHARGE PROTECTION CIRCUIT FOR IMPLANTABLE MEDICAL DEVICE," filed on Jul. 19, 2012, which is hereby incorporated by reference herein in its entirety.

BACKGROUND

Electronic integrated circuits can include many devices, such as thousands or even millions of transistors, resistors, capacitors, interconnections, or other devices. Electrostatically-stored energy, when discharged, can damage integrated circuits such as via electrically overstressing devices included in such circuits. For example, Field Effect Transistors (FETs) or capacitors can be particularly sensitive to ESD events, such as due to a vulnerability of an oxide or other dielectric layer to such ESD events. ESD can occur during manufacturing, during handling, during distribution, during end use of integrated circuits, or in other cases. Equipment, packaging, or humans can electrostatically accumulate and store damaging amounts of such charge, which can then be inadvertently discharged via a pathway through or near the integrated circuit. In one approach, precautionary handling measures can be taken to dissipate electrostatically-stored energy, such as using "grounded" or conductive electrical workstations or packaging, but such measures generally only reduce rather than eliminate the threat of ESD-induced damage to integrated circuits.

OVERVIEW

Generally, an integrated circuit can include one or more bond pads, such as to provide an electrical and mechanical connection to one or more conductors included as a portion of an integrated circuit device package. Such bond pads can be referred to as inputs or outputs (I/Os) and can be coupled to an electrostatic discharge (ESD) clamp circuit included as a portion of the integrated circuit or external to the integrated circuit, such as coupled between a bond pad node and one or more power supply nodes. Such a clamp circuit can, for example, limit an applied voltage applied between a bond pad and a supply node to within a specified voltage range.

In one approach, such as in addition to I/O protection, one or more ESD protection circuits can be included as a portion of the integrated circuit, such as between two or more power supply nodes. An ESD protection circuit can include an active device, such as a transistor, and a sensing circuit, such as including a resistor and a capacitor. Such a sensing circuit can be coupled to a control input of the active device, such as to trigger the active device so that the active device becomes conductive for a duration of an ESD event. For example, such an active device can provide energy dissipation or a shunt pathway for ESD energy, such as between the two or more power supply nodes. An ESD-triggered shunt pathway can prevent electrical overstress of other circuitry coupled to the power supply nodes. In an example of an integrated circuit having multiple power supply nodes (e.g., a "multiple power domain" example), an array of ESD protection circuits can be used to reduce or inhibit electrical overstress, such as due to ESD-induced voltage or other electrical transient applied between respective power supply nodes.

The present inventors have recognized, among other things, that a configuration of a sensing circuit included as a portion of an ESD protection circuit can affect a reliability of the ESD protection circuit. For example, a sensing circuit including a single capacitor can fail, such as due at least in part to a time-dependent dielectric breakdown (TDDB) of the capacitor. TDDB can make the failing capacitor behave as an electrical short circuit. The present inventors have also recognized that a rate of such time-dependent dielectric breakdown can be influenced by an operating voltage (e.g., a "working voltage") applied across a capacitor. For example, a higher working voltage can cause TDDB to occur more rapidly over a lifetime of the capacitor. In an implantable application, including an implantable medical device having one or more integrated circuits, a failure of an ESD protection circuit due to TDDB can cause unwanted effects such as premature battery depletion of the implantable device.

Accordingly, the present inventors have recognized, among other things, that an array including two or more capacitors can be included as a portion of an ESD protection circuit, such as comprising a sensing circuit including two or more capacitors in a series configuration, a parallel configuration, or a combination of series and parallel configurations. Such series, parallel, or series-parallel capacitor configurations can provide redundancy, such as providing reliable ESD protection circuit operation in the presence of one or more of a short circuit capacitor failure (e.g., due to TDDB), an open circuit capacitor failure (e.g., due to an interconnect failure), a "leaky" or "lossy" capacitor failure (e.g., where a capacitor equivalent series resistance or leakage resistance is outside of a specified range), or one or more other failure modes.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 1 illustrates generally an example that can include an electrostatic discharge (ESD) protection circuit, such as can be included as a portion of an integrated circuit included in an implantable medical device.

FIG. 2 illustrates generally an example of an array of ESD protection circuits, such as can be included as a portion of an integrated circuit having multiple "power domains."

FIG. 3 illustrates generally an example that can include an implantable medical device, such as can include a housing and a dielectric header assembly.

DETAILED DESCRIPTION

Figure 4A:
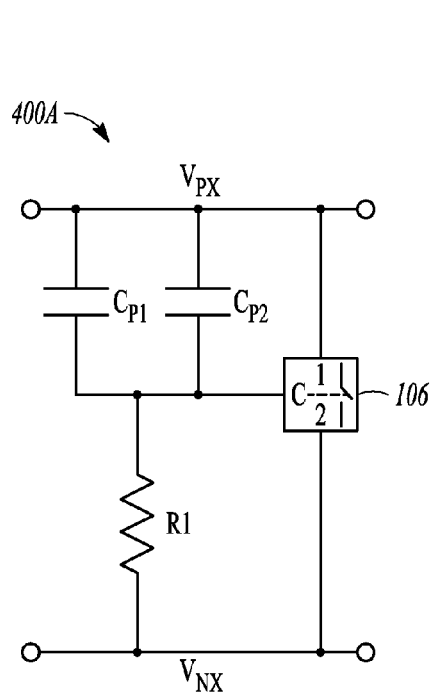
FIG. 4A illustrates generally an example of at least a portion of an ESD protection circuit including a sensing circuit having two or more capacitors in a parallel configuration.

FIG. 1 illustrates generally an example 100 that can include an electrostatic discharge (ESD) protection circuit 102, such as can be included as a portion of an integrated circuit included in an implantable medical device (e.g., an implantable medical device 300 such as shown in FIG. 3). In the example of FIG. 1, the ESD protection circuit 102 can include a first circuit, "$Z_1$," such as a first passive circuit, coupled between a control input, "C," of an active circuit 106, and a first power supply node (e.g., at a voltage $V_P$ with respect to a reference, "REF"). The ESD protection circuit 102 can include a second circuit, "$Z_2$," such as a second passive circuit, coupled between the control input C of the active circuit 106 and a second power supply node (e.g., at a voltage $V_N$ with respect to a reference, "REF"). In an example, $V_N$ can be at a DC potential less than $V_P$, such as at the same potential as REF.

In an example, a combination of the first and second circuits $Z_1$ and $Z_2$ can provide a sensing circuit. The sensing circuit can be configured to trigger the active circuit 106 via the control input C to transition or switch the active circuit 106 from a substantially non-conductive mode (e.g., "cut-off") to a substantially conductive mode (e.g., an "on state"). In this manner, energy such as an ESD voltage transient between $V_P$ and $V_N$ can be clamped, shunted, or otherwise dissipated via the active circuit 106. When triggered, the active circuit 106 via a voltage coupled to the control input C, can protect other "downstream" circuitry 104 that can be coupled to one or more of the first or second power supply nodes $V_P$ or $V_N$. In an example, the active circuit 106 can include one or more transistors or drive circuits, such as shown in the illustrative examples of FIGS. 7A through 7B.

In an example, one or more of the first or second circuits $Z_1$ or $Z_2$ can include one or more passive components such as resistors, capacitors, or inductors. Such passive components can be included as a portion of the integrated circuit 100, such as included in an active implantable medical device. For example, as shown in FIGS. 4A through 4C, or FIG. 5, one or more of $Z_1$ or $Z_2$ can include a capacitor array to enhance a reliability of the ESD protection circuit 102 in the event of a failure of a single capacitor included in the array.

One or more input or output pads, such as a pad 108, can also be protected from ESD events using a clamp circuit 110 coupled between the pad 108 and a respective power supply node, including a first clamp $D_1$ (e.g., a first diode), or a second clamp $D_2$ (e.g., a second diode). Such clamp circuits can be included in addition to the power supply "rail" protection offered by the ESD protection circuit 102.

FIG. 2 illustrates generally an example of an array 200A of ESD protection circuits, such as can be included as a portion of an integrated circuit having multiple "power domains." Generally, if two power supply nodes (e.g., a positive voltage and a reference) are used, then a single ESD protection circuit 102 such as shown in FIG. 1 can be used. If more than two power supply nodes are used (e.g., such as for supplying respective "power domains" in an analog or mixed-mode integrated circuit), an array 200A of protection circuits can be used. For example, a first ESD protection circuit 102A can be coupled between a first supply node $V_1$ and a second supply node $V_2$. A second ESD protection circuit 102B can be coupled between a second supply node $V_2$ and a third supply node $V_3$, and a third ESD protection circuit 102C can be coupled between the third supply node $V_3$ and the first supply node $V_1$. In this manner, an ESD transient coupled between respective power supply nodes (or in common with two power supply nodes) can still be dissipated or shunted by a respective ESD protection circuit 102A, 102B, or 102C. Such an array 200A can be scaled appropriately to accommodate more than three power supply nodes, even though only three nodes are shown in the illustrative example of FIG. 3.

FIG. 3 illustrates generally an example that can include an active implantable medical device (IMD) 300, such as can include a housing 210 and a dielectric portion 220. The IMD 300 can include one or more of an implantable monitor, an implantable pacemaker, an implantable cardioverter-defibrillator (ICD), a cardiac resynchronization therapy (CRT) device, a neurostimulation device, or including one or more other physiologic stimulation, therapy, or monitoring capabilities.

In an example, the IMD 300 can be coupled to one or more implantable lead assemblies, including one or more electrodes located distally with respect to the IMD 300. For example, one or more intravascular or subcutaneously-implanted leads could be coupled to a circuit 200B included in the IMD 300 via a connector block 250 located on or within the dielectric portion 220 (e.g., the dielectric portion 220 and connector block 250 can comprise a "header"). One or more of the housing 210 or a fixed electrode 240 can be included as a portion of the IMD 300, such as coupled to the circuit 200B. The housing 210 can include a hermetically-sealed conductive housing, such as made of titanium. The housing 210 can be electrically connected to the circuit 200B via an electrical coupling 230. The circuit 200B can include an ESD protection circuit 102 such as shown in the examples of FIGS. 1 through 2 or elsewhere, to dissipate electrostatically-stored energy that can be inadvertently coupled to the circuit 200B via one or more of the housing 210, the connector block 250, or the electrode 240. In an example, a reference potential (e.g., a "ground" or "REF" potential) can be established corresponding to a potential of one or more of the housing 210, electrode 240, or connector block 250.

FIG. 4A illustrates generally an example of at least a portion of an ESD protection circuit 400 that can include a sensing circuit having two or more capacitors, such as a first capacitor $C_{P1}$ and a second capacitor $C_{P2}$ in a parallel configuration, and a resistor $R_1$. In FIG. 4A, a time constant can be established at a control input of an active circuit 106, determined by the sum of the parallel capacitances $C_{P1}$ and $C_{P2}$ multiplied by the resistance of resistor $R_1$. Such a sensing circuit configuration can be a high-pass configuration to couple an electrical transient (e.g., an ESD event) occurring between a first power supply node $V_{PX}$ and a second power supply node $V_{NX}$ to a triggering control input, C. If one of $C_{P1}$ or $C_{P2}$ fails in a manner that causes an open circuit, a remaining capacitor can still provide a high-pass configuration, however the time constant can be correspondingly reduced (e.g., shortened in duration corresponding to an increased high-pass cutoff frequency). However, if one of $C_{P1}$ or $C_{P2}$ fails in a manner that causes a short circuit, then the active circuit 106 can be in an undesired continuously-triggered state.

Figure 4B:
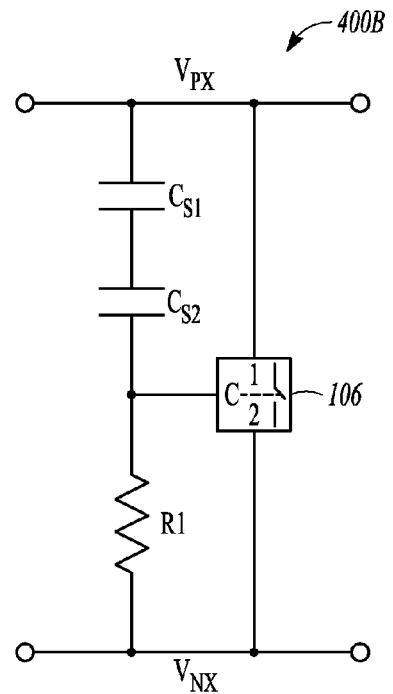
FIG. 4B illustrates generally an example of at least a portion of an ESD protection circuit including a sensing circuit having two or more capacitors in a series configuration.

FIG. 4B illustrates generally an example of at least a portion of an ESD protection circuit 400 that can include a sensing circuit having two or more capacitors, such as a first capacitor $C_{S1}$ and a second capacitor $C_{S2}$ in a series configuration. In FIG. 4B, a time constant can be established at a control input of an active circuit 106, determined by one over the sum of the reciprocals of the series capacitances $C_{S1}$ and $C_{S2}$, multiplied by the resistance of resistor $R_1$. Such a sensing circuit configuration can also provide a high-pass configuration, as in the illustrative example of FIG. 4A. If one of $C_{S1}$ or $C_{S2}$ fails in a manner that causes a short circuit or a low resistance, such as due to TDDB, a remaining capacitor can still provide a high-pass configuration, with a corresponding increase in the time constant (e.g., the time constant can be lengthened, decreasing a high-pass cut-off frequency). In this manner, for short-circuit or low-resistance (e.g. high leakage) capacitor failure modes, the originally-specified high-pass frequency range can be preserved, at the cost that lower frequencies may also trigger the control input in the event of a single capacitor failure. If one of $C_{S1}$ or $C_{S2}$ fails in a manner that causes an open circuit, then the sensing circuit can become inhibited from triggering the control input of the active circuit 106.

Figure 4C:
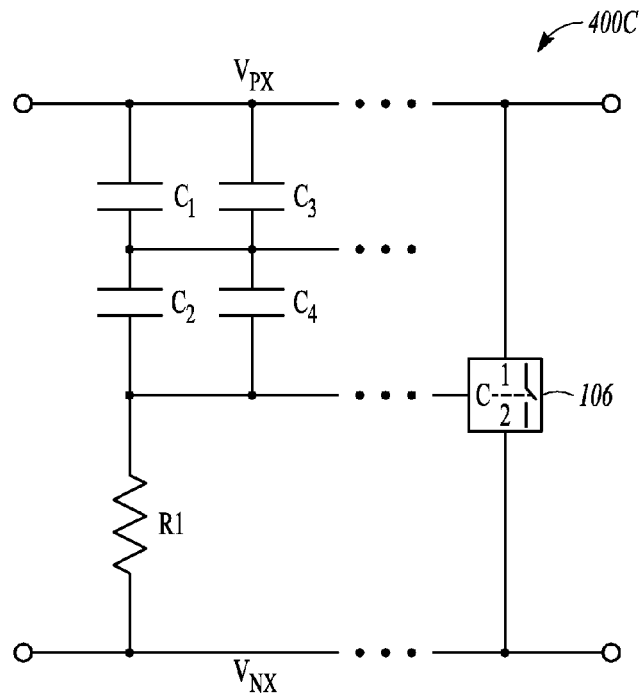
FIG. 4C illustrates generally an example of at least a portion of an ESD protection circuit including a sensing circuit having two or more capacitors in series-parallel configuration.

FIG. 4C illustrates generally an example of at least a portion of an ESD protection circuit 400C that can include a sensing circuit having two or more capacitors in a series and parallel (e.g., a series-parallel) configuration. The present inventors have recognized, among other things, that a capacitor array including both series and parallel capacitors can provide redundancy for both short-circuit and open-circuit failure modes. In an example, the capacitors in the array, such as including first through fourth capacitors, $C_1$ through $C_4$ (or one or more other configurations), can each include a specified capacitance value or working voltage rating. The working voltage rating can be de-rated corresponding to a number of series "rungs" in the array. For example, a specified single (or multiple) short-circuit failure condition need not cause a voltage across a respective capacitor to exceed its corresponding working voltage rating.

In an illustrative example, a voltage difference between a first power supply node $V_{PX}$ and a second power supply node $V_{NX}$ can be about 12 volts. A working voltage range for each capacitor can be specified as in excess of 12 volts. In the example of FIG. 4C, assuming roughly equal series resistances for the capacitors $C_1$ through $C_4$, a voltage of about 6 volts would be dropped across each capacitor during ambulatory operation (e.g., in a non-fault operational scenario). In the event of a single short-circuit failure, 12 volts may be applied across remaining capacitors that are not short-circuited by the failure. For example, if capacitor $C_2$ failed and became short-circuited, the voltage difference between $V_{PX}$ and $V_{NX}$ would be applied across capacitors $C_1$ and $C_3$ (e.g., about 12V would be applied across capacitors $C_1$ and $C_3$, rather than 6V). Capacitor $C_4$ would be bypassed by the short-circuit failure of $C_2$. Capacitors $C_1$ and $C_3$ can still operate reliably, being rated for at least 12V in this illustrative example. Redundancy can also be provided such as by using different capacitor dielectric materials or capacitor configurations for respective capacitors, as shown in the illustrative example of FIG. 6.

Figure 5:
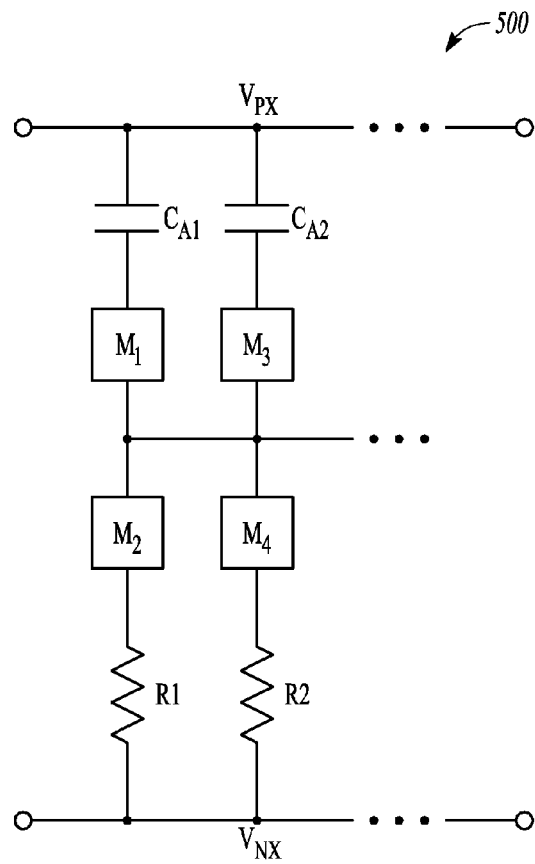
FIG. 5 illustrates generally an example of at least a portion of a sensing circuit that can be included as a portion of an ESD protection circuit, such as can include one or more metal features that can be used to select a desired capacitance or resistance, such as using a metal-only mask adjustment.

FIG. 5 illustrates generally an example of at least a portion of a sensing circuit that can be included as a portion of an ESD protection circuit, that can include one or more conductive features $M_1$ through $M_4$, an array of capacitors, such as including a first capacitor $C_{A1}$ or a second capacitor $C_{A2}$, or an array of resistors, such as a first resistor $R_1$ or a second resistor $R_2$. The conductive features $M_1$ through $M_4$ can include metal or one or more other conductive materials that can be used to select a desired capacitance or resistance, such as using a metal-only mask adjustment before or during fabrication of an integrated circuit. For example, a desired time constant (as discussed in the examples of FIG. 1, 2, or 4A through 4C) can be selected for the sensing circuit by including or omitting various conductive (e.g., metallization layer) features $M_1$ through $M_4$, without requiring modification of other layers of an integrated circuit.

Figure 6:
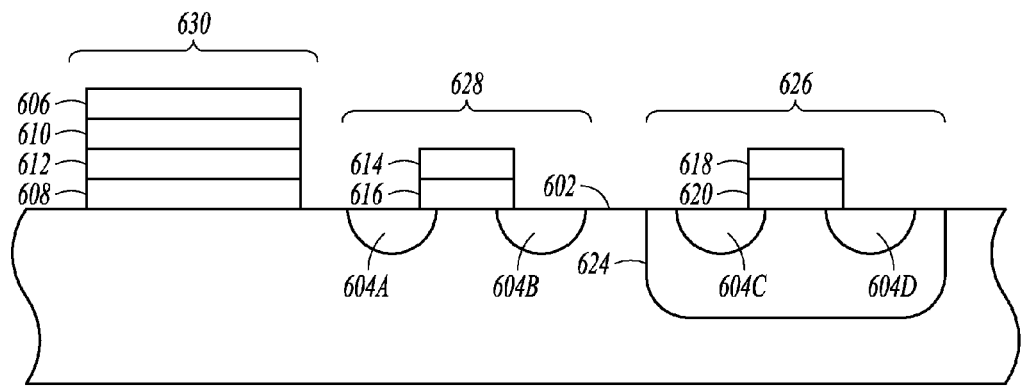
FIG. 6 illustrates generally a section view of at least a portion of an integrated circuit that can include two or more capacitor devices, and a field-effect transistor (FET) device, such as can be included as a portion of an implantable medical device.

FIG. 6 illustrates generally a section view of at least a portion of an integrated circuit 600 that can include two or more capacitors, or a field-effect transistor (FET) device, that can be included as a portion of an implantable medical device. The FET device 628 can be included as a portion of the active circuit 106 as discussed in the examples of above and elsewhere. For example, the FET device 628 can include respective first and second well regions 604A and 604B, including a conductivity type opposite the type of the substrate 602 (or, in an example, opposite the conductivity type of a larger well or epitaxially-grown region surrounding the FET device 628). Such well regions 604A and 604B can be specified as source or drain regions. A gate dielectric 616 can be formed, such as slightly laterally overlapping with a portion of the well regions 604A and 604B. A conductive terminal such as a metal or polysilicon terminal can be formed on the gate 616 dielectric to provide a gate terminal 614. One or more of the well regions 604A and 604B, or the gate terminal 614 can be electrically coupled to other portions of the integrated circuit 600, such as to provide an ESD protection circuit as discussed in other examples above or below.

In the illustrative example of FIG. 6, a first capacitor can include a poly-poly capacitor 630, comprising a first polysilicon terminal 612 (or including one or more other conductive materials) grown or deposited on a dielectric layer 608 (e.g., silicon dioxide ($SiO_2$) or including one or more other materials). Such a dielectric layer 608 can be located upon or can comprise a portion of a semiconductor substrate 602. A capacitor dielectric material 610 can be formed on the first polysilicon terminal 612, using a chemical vapor deposition technique, a spin-on technique, a sputtering technique, or using one or more other techniques. A second polysilicon terminal 606 can be formed, for example, opposite (e.g., above, as shown in FIG. 6) the first polysilicon terminal 612, with the capacitor dielectric material 610 separating the first and second polysilicon terminals 612 and 606.

A second capacitor can include a dielectric-on-monocrystalline-silicon configuration 626. For example, the substrate 602 can include a first conductivity type, such as a positive (p-type) doping impurity. A well region 624 can include an n-type or p-type doping impurity. The second capacitor can include a thermally-grown or "native" oxide layer 620 formed on the substrate 602, such as in a manner similar to a gate dielectric 616 formed as a portion of the FET device 628. The second capacitor including the dielectric-on-monocrystalline-silicon configuration 626 can include respective first and second well regions 604C and 604D, such as including an n-type or p-type doping impurity. Growth of the oxide layer 620 on a monocrystalline region can reduce or inhibit defect propagation into the oxide layer 620, providing reduced susceptibility to TDDB as compared to the poly-poly capacitor 630. Unlike the poly-poly capacitor 630, the dielectric-on-monocrystalline-silicon configuration 626 can be fabricated as an enhancement-mode or depletion-mode device, and a capacitance can be dependent, such as non-linearly dependent, on a polarity and a magnitude of a voltage applied between the substrate 602 and a terminal 618 of the dielectric-on-monocrystalline-silicon configuration 626.

An array of capacitors can be formed, such as via using one or more capacitors including the poly-poly capacitor 630 configuration, or the dielectric-on-monocrystalline-silicon configuration 626, or using one or more other configurations. One or more conductive layers (e.g., one or metallization layers) can be formed or deposited to provide electrical interconnections between one or more of the poly-poly capacitor 630, the FET device 628, or the second capacitor in the dielectric-on-mono crystalline-silicon configuration 626.

Figure 7A:
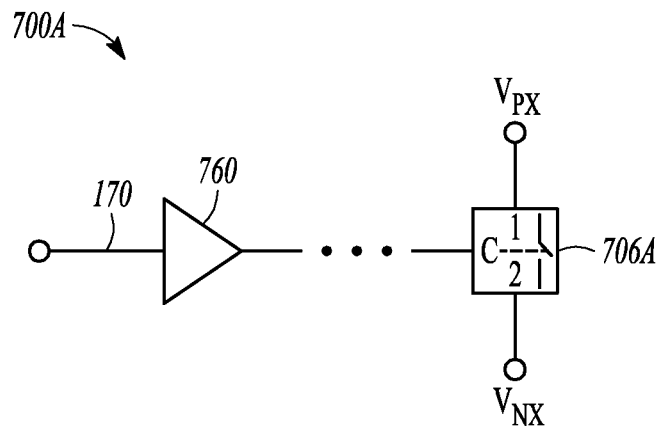
FIG. 7A illustrates generally an example of at least portion of an ESD protection circuit that can include an active circuit comprising a shunt device and a drive circuit.

FIG. 7A illustrates generally an example of at least a portion of an ESD protection circuit 700A that can include an active circuit 706A comprising a shunt device and a drive circuit 760. As discussed in other examples above, the active circuit 106 of FIG. 1 or 2 need not be a single device. For example, a FET device 628 as shown in FIG. 6 can be specified to reliably shunt multiple ESD events without degradation. One or more other active circuits can be used, such as one or more of a bipolar junction transistor, a junction FET, or an IGBT.

Accordingly, in an example, one or more drive circuits can be used, such as coupled to a control input (e.g., a gate) of the active circuit 706A to reliably trigger the active circuit 706A into a conductive mode during an ESD event. Such a drive circuit can include one or more transistors, such as a complementary transistor pair as shown in the illustrative example of FIG. 7B. Other configurations can be used, such as one or more inverting or non-inverting drive configurations. For example, in an inverting configuration, an input 170 can trigger the active circuit 706A in response to voltage transition from a higher voltage to a lower voltage. In such an inverting example, the locations of the capacitors in the examples of FIGS. 4A through 4C or FIG. 5 would be exchanged with resistors, and the locations with resistors would be exchanged with capacitors. Generally, whether the drive circuit 760 is inverting or non-inverting, the active circuit 706A (e.g., the shunt device) can be in a non-conducting mode during ambulatory operation and can be switched into a conducting mode and held in such a conducting mode by the drive circuit 760 for at least a duration of an ESD event.

Figure 7B:
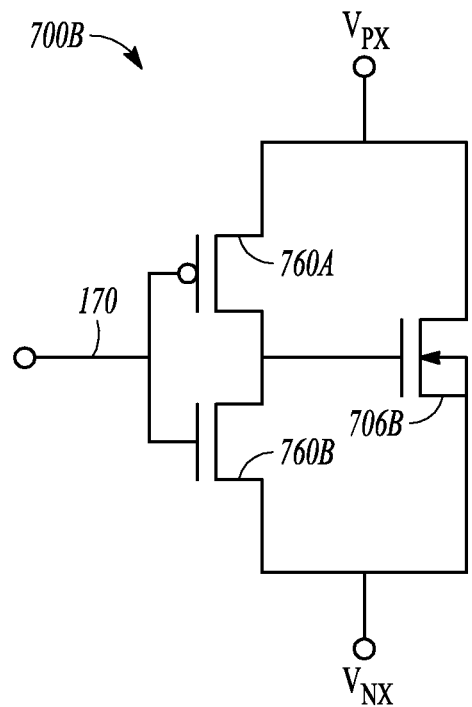
FIG. 7B illustrates generally an example of at least a portion of ESD protection circuit that can include a FET shunt device, and a complementary FET drive circuit.

FIG. 7B illustrates generally an example of at least a portion of ESD protection circuit that can include a FET shunt device 706B and a complementary FET drive circuit including a first FET device 760A having a first conductivity type (e.g., a PMOS device) and a second FET device 760B having a second conductivity type (e.g., an NMOS device). In the example of FIG. 7B, the drive circuit can include an inverting configuration, triggering the shunt device 706B in response to a voltage transition from a higher voltage to a lower voltage passing through a specified voltage threshold.

Figure 8:
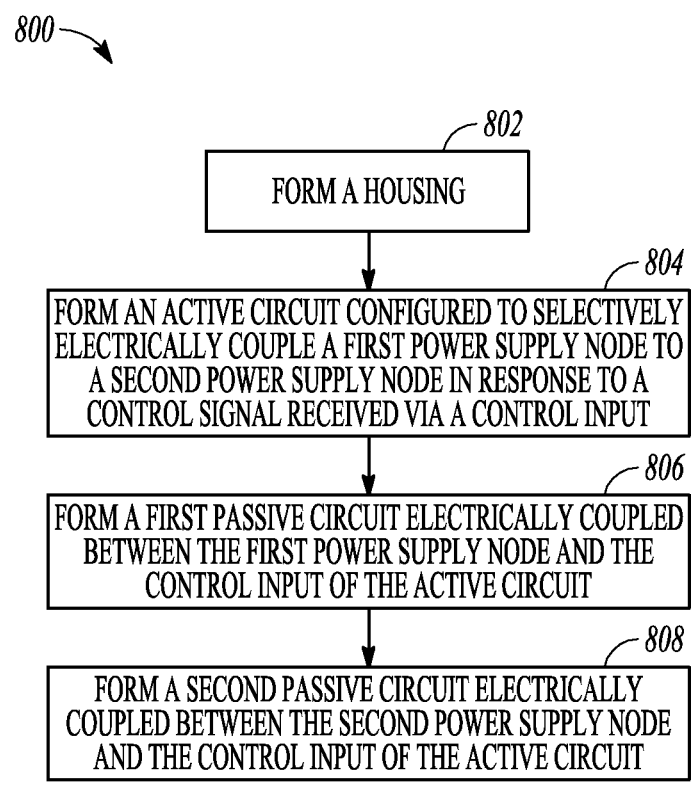
FIG. 8 illustrates generally a technique, such as a method, that can include forming an integrated circuit such as for an implantable medical device.

FIG. 8 illustrates generally a technique 800, such as a method, that can include forming a housing of an implantable medical device (IMD), at 802, and forming circuits that can be placed in the housing, such as a portion of an ESD protection circuit discussed in the examples of FIGS. 1, 2, 3, 4A through 4C, 5, 6, 7A through 7B, or elsewhere. For example, at 804, an active circuit can be formed, including one or more transistors, the active circuit configured to selectively electrically couple a first power supply node to a second power supply node in response to a control signal received via a control input.

At 806, a first passive circuit can be formed, the first passive circuit electrically coupled between the first power supply node and the control input of the active circuit. At 808, a second passive circuit can be formed. The second passive circuit can be electrically coupled between the second power supply node and the control input of the active circuit. In an example, at least one of forming the first or second passive circuits includes forming an array of capacitors in a series configuration, a parallel configuration, or a combination of series and parallel configurations. In an example, the first and second passive circuits can be configured to establish a specified time constant, and, in response to an applied ESD, the first and second passive circuits can be configured to provide the control signal to the control input using the specified time constant, and the active circuit can be configured to switch from a substantially non-conductive mode to a substantially conductive mode in response to the control signal to provide a shunt path for the applied ESD between the first and second power supply nodes.

VARIOUS NOTES & EXAMPLES

Example 1 can include or use subject matter (e.g., an apparatus, a method, a means for performing acts, or a device readable medium including instructions that, when performed by the device, can cause the device to perform acts), which can include or an implantable medical device, comprising a housing, an integrated circuit included in the housing, the integrated circuit comprising an electrostatic discharge (ESD) protection circuit including an active circuit configured to selectively electrically couple a first power supply node to a second power supply node in response to a control signal received via a control input, a first passive circuit electrically coupled between the first power supply node and the control input of the active circuit, a second passive circuit electrically coupled between the second power supply node and the control input of the active circuit, at least one of the first or second passive circuits including an array of capacitors in a series configuration, a parallel configuration, or a combination of series and parallel configurations. In Example 1, the first and second passive circuits are configured to establish a specified time constant, and, in response to an applied ESD, the first and second passive circuits are configured to provide the control signal to the control input using the specified time constant, and the active circuit is configured to switch from a substantially non-conductive mode to a substantially conductive mode in response to the control signal to provide a shunt path for the applied ESD between the first and second power supply nodes.

Example 2 can include, or can optionally be combined with the subject matter of Example 1, to optionally include a first passive circuit including an array of capacitors in a series and parallel configuration, the second passive circuit including a resistor.

Example 3 can include, or can optionally be combined with the subject matter of one or any combination of Examples 1 or 2 to optionally include at least one of the first or second passive circuits including an array of at least two capacitors in a series configuration.

Example 4 can include, or can optionally be combined with the subject matter of one or any combination of Examples 1 through 3 to optionally include at least one of the first or second passive circuits including an array of at least two capacitors in a parallel configuration.

Example 5 can include, or can optionally be combined with the subject matter of one or any combination of Examples 1 through 4 to optionally include a first capacitor included in one or more of the first or second passive circuits comprising a capacitor dielectric including a dielectric on a monocrystalline region of an integrated circuit substrate.

Example 6 can include, or can optionally be combined with the subject matter of Example 5, to optionally include a second capacitor included in one or more of the first or second passive circuits comprising a capacitor dielectric located between polysilicon regions of an integrated circuit.

Example 7 can include, or can optionally be combined with the subject matter of one or any combination of Examples 1 through 6 to optionally include an active circuit comprising a shunt Field Effect Transistor (FET) configured to the couple the first power supply node to the second power supply node.

Example 8 can include, or can optionally be combined with the subject matter of Example 7, to optionally include an active circuit comprising a drive circuit coupled to a gate of the shunt FET, the control input comprising an input of the drive circuit.

Example 9 can include, or can optionally be combined with the subject matter of Example 8, to optionally include a drive circuit comprising a complementary transistor pair.

Example 10 can include, or can optionally be combined with the subject matter of one or any combination of Examples 1 through 9 to optionally include a first power supply node comprising a first DC supply voltage, the second power supply node comprising a second DC supply voltage, the first DC supply voltage positive in polarity with respect to the second DC supply voltage.

Example 11 can include, or can optionally be combined with the subject matter of Example 10, to optionally include a second power supply node comprising a reference node.

Example 12 can include, or can optionally be combined with the subject matter of Example 11, to optionally include a conductive housing, the reference node electrically coupled to the housing.

Example 13 can include, or can optionally be combined with the subject matter of Example 12, to optionally include a dielectric portion coupled to the housing, the dielectric portion including an electrode on or within the dielectric portion, the integrated circuit comprising a bond pad, the electrode electrically coupled to the bond pad; the integrated circuit comprising at least one ESD clamp circuit between the bond pad an at least one power supply node.

Example 14 can include, or can optionally be combined with the subject matter of one or any combination of Examples 1 through 13 to include, subject matter (e.g., an apparatus, a method, a means for performing acts, or a machine readable medium including instructions that, when performed by the machine, that can cause the machine to perform acts), which can include an implantable medical device, comprising a housing, an integrated circuit included in the housing, the integrated circuit comprising an electrostatic discharge (ESD) protection circuit including an active circuit configured to selectively electrically couple a first power supply node to a second power supply node in response to a control signal received via a control input, a first passive circuit electrically coupled between the first power supply node and the control input of the active circuit, a second passive circuit electrically coupled between the second power supply node and the control input of the active circuit, the first passive circuit including an array of capacitors in a series and parallel configuration, the second passive circuit including a resistor, the first and second passive circuits configured to establish a specified time constant, and, in response to an applied ESD, the first and second passive circuits configured to provide the control signal to the control input using the specified time constant, the active circuit configured to switch from a substantially non-conductive mode to a substantially conductive mode in response to the control signal to provide a shunt path for the applied ESD between the first and second power supply nodes, a first capacitor included in one or more of the first or second passive circuits including a capacitor dielectric comprising a dielectric on a monocrystalline region of an integrated circuit substrate, and a second capacitor included in one or more of the first or second passive circuits including a capacitor dielectric located between polysilicon regions of an integrated circuit.

Example 15 can include, or can optionally be combined with the subject matter of one or any combination of Examples 1 through 14 to include, subject matter (e.g., an apparatus, a method, a means for performing acts, or a machine readable medium including instructions that, when performed by the machine, that can cause the machine to perform acts), such as can include a method for providing electrostatic discharge (ESD) protection in an implantable medical device, the method comprising forming a housing, forming an integrated circuit in the housing, the integrated circuit including an electrostatic discharge (ESD) protection circuit, the forming the integrated circuit comprising forming an active circuit configured to selectively electrically couple a first power supply node to a second power supply node in response to a control signal received via a control input, forming a first passive circuit electrically coupled between the first power supply node and the control input of the active circuit, forming a second passive circuit electrically coupled between the second power supply node and the control input of the active circuit, at least one of forming the first or second passive circuits including forming an array of capacitors in a series configuration, a parallel configuration, or a combination of series and parallel configurations, the first and second passive circuits configured to establish a specified time constant, and, in response to an applied ESD, the first and second passive circuits configured to provide the control signal to the control input using the specified time constant, and the active circuit configured to switch from a substantially non-conductive mode to a substantially conductive mode in response to the control signal to provide a shunt path for the applied ESD between the first and second power supply nodes.

Example 16 can include, or can optionally be combined with the subject matter of Example 15, to optionally include forming the first passive circuit including forming an array of capacitors in a series and parallel configuration, and forming the second passive circuit includes forming a resistor.

Example 17 can include, or can optionally be combined with the subject matter of one or any combination of Examples 15 or 16 to optionally include forming at least one of the first or second passive circuits including forming an array of at least two capacitors in a series configuration.

Example 18 can include, or can optionally be combined with the subject matter of one or any combination of Examples 15 through 17 to optionally include forming at least one of the first or second passive circuits including forming an array of at least two capacitors in a parallel configuration.

Example 19 can include, or can optionally be combined with the subject matter of one or any combination of Examples 15 through 18 to optionally include forming a first capacitor included in one or more of the first or second passive circuits including forming a capacitor dielectric comprising a dielectric on a monocrystalline region of an integrated circuit substrate.

Example 20 can include, or can optionally be combined with the subject matter of one or any combination of Examples 15 through 19 to optionally include forming a second capacitor included in one or more of the first or second passive circuits including forming a capacitor dielectric located between polysilicon regions of an integrated circuit.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An implantable medical device, comprising:
a housing;
an integrated circuit included in the housing, the integrated circuit comprising an electrostatic discharge (ESD) protection circuit including:
an active circuit configured to selectively electrically couple a first power supply node to a second power supply node in response to a control signal received via a control input of the active circuit, the active circuit including a drive circuit or a complementary transistor pair coupled to the control input;
a first passive circuit electrically coupled between the first power supply node and the control input of the active circuit; and
a second passive circuit electrically coupled between the second power supply node and the control input of the active circuit;
wherein at least one of the first or second passive circuits includes an array of capacitors in a series configuration, a parallel configuration, or a combination of series and parallel configurations;
wherein the first and second passive circuits are configured to establish a specified time constant, and, in response to an applied ESD, the first and second passive circuits are configured to provide the control signal to the control input using the specified time constant; and
wherein the active circuit is configured to switch from a substantially non-conductive mode to a substantially conductive mode in response to the control signal to provide a shunt path for the applied ESD between the first and second power supply nodes.

2. The implantable medical device of claim 1, wherein the first passive circuit includes an array of capacitors in a series and parallel configuration; and
wherein the second passive circuit includes a resistor.

3. The implantable medical device of claim 1, wherein at least one of the first or second passive circuits includes an array of at least two capacitors in a series configuration.

4. The implantable medical device of claim 1, wherein at least one of the first or second passive circuits includes an array of at least two capacitors in a parallel configuration.

5. The implantable medical device of claim 1, wherein a first capacitor included in one or more of the first or second passive circuits includes a capacitor dielectric comprising a dielectric on a monocrystalline region of an integrated circuit substrate.

6. The implantable medical device of claim 5, wherein a second capacitor included in one or more of the first or second passive circuits includes a capacitor dielectric located between polysilicon regions of an integrated circuit.

7. The implantable medical device of claim 1, wherein the active circuit includes a shunt Field Effect Transistor (FET) configured to couple the first power supply node to the second power supply node.

8. The implantable medical device of claim 7, wherein the active circuit includes a drive circuit coupled to a gate of the shunt FET; and
wherein the control input comprises an input of the drive circuit.

9. The implantable medical device of claim 8, wherein the drive circuit includes a complementary transistor pair.

10. The implantable medical device of claim 1, wherein the first power supply node includes a first DC supply voltage;
wherein the second power supply node includes a second DC supply voltage; and
wherein the first DC supply voltage is positive in polarity with respect to the second DC supply voltage.

11. The implantable medical device of claim 10, wherein the second power supply node comprises a reference node.

12. The implantable medical device of claim 11, comprising a conductive housing; and
wherein the reference node is electrically coupled to the housing.

13. The implantable medical device of claim 12, comprising a dielectric portion coupled to the housing, the dielectric portion including an electrode on or within the dielectric portion;
wherein the integrated circuit comprises a bond pad;
wherein the electrode is electrically coupled to the bond pad; and
wherein the integrated circuit comprises at least one ESD clamp circuit between the bond pad and at least one power supply node.

14. An implantable medical device, comprising:
a housing;
an integrated circuit included in the housing, the integrated circuit comprising an electrostatic discharge (ESD) protection circuit including:
an active circuit configured to selectively electrically couple a first power supply node to a second power supply node in response to a control signal received via a control input;
a first passive circuit electrically coupled between the first power supply node and the control input of the active circuit; and
a second passive circuit electrically coupled between the second power supply node and the control input of the active circuit;
wherein the first passive circuit includes an array of capacitors in a series and parallel configuration;
wherein the second passive circuit includes a resistor;
wherein the first and second passive circuits are configured to establish a specified time constant, and, in response to an applied ESD, the first and second passive circuits are configured to provide the control signal to the control input using the specified time constant;
wherein the active circuit is configured to switch from a substantially non-conductive mode to a substantially conductive mode in response to the control signal to provide a shunt path for the applied ESD between the first and second power supply nodes;
wherein a first capacitor included n one or more of the first or second passive circuits includes a capacitor dielectric comprising a dielectric on a monocrystalline region of an integrated circuit substrate; and
wherein a second capacitor included in one or more of the first or second passive circuits includes a capacitor dielectric located between polysilicon regions of an integrated circuit.

15. A method for providing electrostatic discharge (ESD) protection in an implantable medical device, the method comprising:
forming a housing;
forming an integrated circuit in the housing, the integrated circuit including an electrostatic discharge (ESD) protection circuit, the forming the integrated circuit comprising:
forming an active circuit configured to selectively electrically couple a first power supply node to a second power supply node in response to a control signal received via a control input of the active circuit, wherein forming the active circuit includes forming a drive circuit or a complementary transistor pair coupled to the control input;
forming a first passive circuit electrically coupled between the first power supply node and the control input of the active circuit; and
forming a second passive circuit electrically coupled between the second power supply node and the control input of the active circuit;
wherein at least one of forming the first or second passive circuits includes forming an array of capacitors in a series configuration, a parallel configuration, or a combination of series and parallel configurations;
wherein the first and second passive circuits are configured to establish a specified time constant, and, in response to an applied ESD, the first and second passive circuits are configured to provide the control signal to the control input using the specified time constant; and
wherein the active circuit is configured to switch from a substantially non-conductive mode to a substantially conductive mode in response to the control signal to provide a shunt path for the applied ESD between the first and second power supply nodes.

16. The method of claim 15, wherein forming the first passive circuit includes forming an array of capacitors in a series and parallel configuration; and
wherein forming the second passive circuit includes forming a resistor.

17. The method of claim 15, wherein forming at least one of the first or second passive circuits includes forming an array of at least two capacitors in a series configuration.

18. The method of claim 15, wherein forming at least one of the first or second passive circuits includes forming an array of at least two capacitors in a parallel configuration.

19. The method of claim 15, wherein forming a first capacitor included in one or more of the first or second passive circuits includes forming a capacitor dielectric comprising a dielectric on a monocrystalline region of an integrated circuit substrate.

20. The method of claim 15, wherein forming a second capacitor included in one or more of the first or second passive circuits includes forming a capacitor dielectric located between polysilicon regions of an integrated circuit.

* * * * *